United States Patent
White

(10) Patent No.: US 7,847,135 B1
(45) Date of Patent: Dec. 7, 2010

(54) PROPYLENE OXIDE ISOMERIZATION PROCESS

(75) Inventor: Daniel F. White, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 12/589,932

(22) Filed: Oct. 30, 2009

(51) Int. Cl.
*C07C 33/02* (2006.01)

(52) U.S. Cl. .................. 568/907; 568/908; 568/909.5

(58) Field of Classification Search .................. 568/907, 568/908, 909.5
See application file for complete search history.

(56) References Cited

U.S. PATENT DOCUMENTS

| | | |
|---|---|---|
| 2,426,264 A | 8/1947 | Fowler et al. |
| 2,986,585 A | 5/1961 | Denton |
| 3,044,850 A | 7/1962 | Denton |
| 3,238,264 A | 3/1966 | Rowton |
| 3,274,121 A | 9/1966 | Schneider |
| 4,215,077 A | 7/1980 | Matsumoto et al. |
| 4,342,666 A | 8/1982 | Hardy, Sr. |
| 4,720,598 A | 1/1988 | Scholte |
| 5,262,371 A | 11/1993 | Faraj |
| 5,444,141 A | 8/1995 | Guo |
| 6,803,491 B1 | 10/2004 | Shum |

*Primary Examiner*—Sikarl A Witherspoon
(74) *Attorney, Agent, or Firm*—Kevin M. Carroll

(57) ABSTRACT

The invention is a process to produce allyl alcohol from propylene oxide. The process comprises isomerizing propylene oxide in the presence of a lithium phosphate catalyst which contains boron and from 2000 to 4000 ppm sodium. The propylene oxide conversion is 37 percent or lower.

9 Claims, No Drawings

PROPYLENE OXIDE ISOMERIZATION PROCESS

FIELD OF THE INVENTION

The invention relates to isomerizing propylene oxide to produce allyl alcohol.

BACKGROUND OF THE INVENTION

Allyl alcohol is used commercially for the manufacture of 1,4-butanediol (see, to for example, U.S. Pat. No. 4,215,077). It is also used as a hydroxyl functional monomer in the polymer industry (see, for example, U.S. Pat. No. 5,444,141).

Allyl alcohol can be produced by the isomerization of propylene oxide (PO). PO isomerization can be performed by a slurry-phase process (see for example, U.S. Pat. No. 3,274,121) or by a gas-phase process (see, e.g., U.S. Pat. No. 3,044,850).

Isomerization is typically performed in the presence of a lithium phosphate catalyst. The preparation of lithium phosphate catalysts is well known in the art. U.S. Pat. No. 2,426,264 teaches preparing the catalyst by precipitating a crude lithium phosphate from the mixture of an aqueous solution that contains phosphate ions and an aqueous solution that contains lithium ions. The crude precipitate is then washed with water and dried to form catalyst powder.

Methods for improving lithium phosphate catalysts are known. U.S. Pat. No. 2,986,585 teaches adding alkali metal hydroxides such as sodium hydroxide and potassium hydroxide during the precipitation of lithium phosphate. The resultant catalyst has improved activity and selectivity for allyl alcohol production. U.S. Pat. No. 6,803,491 teaches a further improvement to lithium phosphate catalysts, which comprises precipitating a lithium phosphate from a mixture comprising a first aqueous solution containing lithium and sodium ions and a second aqueous solution containing phosphate and borate ions. The resultant lithium phosphate catalyst has increased activity and selectivity in the isomerization of an alkylene oxide to the corresponding allylic alcohol. The lithium phosphate catalyst is taught to preferably contain from about 0.01 wt. % to about 1 wt. % of sodium, more preferably from about 0.02 wt. % to about 0.8 wt. % of sodium.

As with any chemical process, it is desirable to attain still further improvements in the PO isomerization process. We have discovered a new process for the production of allyl alcohol.

SUMMARY OF THE INVENTION

The invention is a process to produce allyl alcohol from propylene oxide. The process comprises isomerizing propylene oxide in the presence of a lithium phosphate catalyst at a propylene oxide conversion of 37 percent or lower. The lithium phosphate catalyst contains boron and 2000 to 4000 ppm sodium.

DETAILED DESCRIPTION OF THE INVENTION

The process of the invention comprises isomerizing propylene oxide in the presence of a catalyst to produce allyl alcohol, wherein the propylene oxide conversion is 37 percent or lower. The catalyst of the invention is a lithium is phosphate catalyst, containing boron and 2000 to 4000 ppm sodium. Lithium phosphate catalysts are well known in the art, and can be produced by the process of U.S. Pat. No. 6,803,491.

The lithium phosphate can be produced, for example, by mixing an aqueous Li—Na solution which contains lithium and sodium ions and an aqueous P—B solution which contains phosphate and borate ions. The aqueous Li—Na solution is preferably prepared by dissolving a lithium compound and a sodium compound in water. The Li—Na solution preferably has a lithium ion concentration that is within the range of 1.0 M to 3.5 M, and more preferably from 1.5 M to 3.0 M. The sodium ion concentration is preferably within the range of 0.5 M to 2.0 M, and more preferably from 0.75 M to 1.5 M. Preferable lithium compounds for use in the Li—Na solution include lithium hydroxide, lithium nitrate, lithium acetate, and mixtures thereof. Lithium hydroxide is particularly preferred. Preferable sodium compounds include sodium hydroxide, sodium nitrate, sodium acetate, sodium carbonate, and mixtures thereof. Sodium hydroxide is particularly preferred.

The aqueous P—B solution is preferably prepared by dissolving a phosphate compound and a borate compound in water. The P—B solution preferably has a phosphate ion concentration that is within the range of 0.5 M to 1.5 M, and more preferably from 0.5 M to 1.0 M. Preferable phosphate compounds include sodium phosphates, potassium phosphates, ammonium phosphates and mixtures thereof. Sodium phosphates are particularly preferred. The borate ion concentration is preferably within the range of 0.5 M to 2.5 M, more preferably from 1.0 M to 2.0 M. Preferable borate compounds include boric acid, sodium borates, potassium borates, ammonium borates and mixtures thereof. Boric acid, sodium borates, and their hydrates are particularly preferred.

When a sodium phosphate is used as the phosphate compound for forming the P—B solution, it is not necessary to add a sodium compound to produce the Li—Na solution. Thus, when sodium phosphate is the source of phosphate ions, a Li solution only can be used in place of the Li—Na solution.

Following formation, the Li—Na and P—B solutions are mixed to produce a reaction mixture from which crude lithium phosphate will precipitate. Prior to mixing, the Li—Na and the P—B solutions are both preferably heated to a temperature within the range of 45° C. to 95° C. More preferably, the solutions are heated to a temperature within the range of 60° C. to 80° C. The mixing can be performed in a reactor or any suitable containers. Preferably, the Li:P molar ratio in the reaction mixture is within the range of 1 to 6, and more preferably, within the range of 2 to 4.

Upon mixing, a crude lithium phosphate precipitates. The precipitate is isolated and washed with sufficient water to obtain a washed lithium phosphate that contains desirable amounts of sodium and boron.

The lithium phosphate catalyst useful in the process of the invention contains from 2000 to 4000 ppm of sodium, preferably from 2500 to 3500 ppm of sodium. The lithium phosphate of the invention preferably contains from 0.03 wt. % to 1 wt. % of boron, and more preferably from 0.1 wt. % to 0.8 wt. % of boron.

Depending upon the isomerization reaction conditions, the lithium phosphate catalyst may be used as a powder or may be spray dried, pelletized or extruded prior to use in isomerization. If spray dried, pelletized or extruded, the lithium phosphate may additionally comprise a binder (e.g., alumina or silica) or the like and may be molded, spray dried, shaped or extruded into any desired form.

The process of the invention comprises isomerizing propylene oxide to produce allyl alcohol. Isomerization processes are known, which include slurry and gas-phase (also called vapor-phase) processes. For instance, U.S. Pat. Nos.

3,238,264, 3,274,121, and 4,342,666 teach slurry-phase isomerization, and U.S. Pat. Nos. 4,720,598, 5,262,371, and 5,455,215 teach gas-phase isomerization. The teachings of these patents are incorporated herein by reference.

It is preferred to perform the isomerization in the slurry phase. In the slurry-phase process, a catalyst slurry is formed by suspending the lithium phosphate catalyst in an inert liquid. Preferably, lithium phosphate is used in the powder form when used in the slurry phase. Preferably the weight ratio of catalyst to inert liquid is in the range of 0.05 to 0.7.

Propylene oxide is then passed through the slurry at elevated temperature to produce allyl alcohol. Preferably, the propylene oxide is vaporized by a pre-heating step prior to the isomerization reaction. The allyl alcohol product exits the slurry-phase reactor as a vapor stream.

The inert liquid used in the slurry may be any suitable hydrocarbon or mixture thereof which will remain liquid, and is non-reactive and thermally stable, at the reaction temperatures and pressures employed. Preferably, the slurry-phase isomerization is performed at a temperature within the range of 200° C. to 300° C., and more preferably at a temperature within the range of 240° C. to 280° C. Therefore, the inert liquid is preferably a high boiling, high molecular weight (typically MW is greater than 120) hydrocarbon, or mixtures thereof. More preferably, the inert liquid is a $C_{12}$ or greater alkylaromatic hydrocarbon such as dodecyl benzene or a mixture of alkylaromatic hydrocarbons such as $C_{14-30}$ alkylaromatic hydrocarbons (e.g., Therminol® 55 a product of Solutia, Inc.).

The process may also be performed in the gas phase. In the gas phase, propylene oxide is passed through a lithium phosphate catalyst bed at elevated temperatures, and the allyl alcohol product is formed. The catalyst used in the gas phase is preferably spray dried, pelletized or extruded prior to use. The gas-phase process is performed at temperatures preferably within the range of 150° C. to 400° C., more preferably from 180° C. to 360° C., and most preferably from 270° C. to 320° C. The allyl alcohol product exits the gas-phase reactor as a vapor stream.

In the gas-phase process, the catalyst particles are preferably contained in a packed bed or multiple tubes, using a heat transfer gas or liquid to control temperature to minimize over-heating or the development of hot spots.

If desired, an inert gas may be used as a diluent for the propylene oxide in the gas-phase process. Thus, for example, a mixed vapor stream of propylene oxide and nitrogen can be fed to the reaction zone. Suitable inert gases include nitrogen, argon, helium, and the like, and mixtures thereof.

The process of the invention can be performed at any suitable pressure, and is most conveniently performed at or slightly above atmospheric pressure.

Following isomerization, the allyl alcohol product is recovered and purified from unreacted propylene oxide, reactant gases, and other by-products. The recovery and purification is preferably performed in one or more distillation columns.

The propylene oxide conversion is calculated by the equation: (moles PO reacted)/(moles PO fed)×100.

Several side reactions compete with the desired isomerization, leading to the formation of by-products such as propionaldehyde, acetone, n-propyl alcohol and acrolein. Selectivity of allyl alcohol formation is calculated by the equation: (moles allyl alcohol produced)/(moles PO reacted)×100.

The process of the invention is characterized by a propylene oxide conversion of 37 percent or lower, preferably at 35 percent or lower. I have found that the amount of sodium in the catalyst is important when running the propylene oxide isomerization process of the invention at low conversion of 37 percent or lower. Catalysts having sodium content within the range of 2000 to 4000 ppm maintain high selectivity at PO conversion both higher and lower than 37 percent, whereas catalysts having sodium content outside the range show decreased allyl alcohol selectivity when run at lower PO conversion.

The capability of maintaining high selectivity at lower PO conversion allows for significant flexibility in the PO isomerization process. Running at lower PO conversion is sometimes necessary when allyl alcohol demand is lower, or may be desired to reduce the energy requirements that are associated with running isomerization at higher conversions and higher temperatures.

The following examples merely illustrate the invention. Those skilled in the art will recognize many variations that are within the spirit of the invention and scope of the claims.

Example 1

Preparation of Lithium Phosphate Catalysts

Catalyst 1A (2800 ppm Na): Lithium phosphate containing 2800 ppm sodium is prepared by dissolving sodium phosphate (380 g, 1 mole) and boric acid (53 g) in 1 L of water at 70° C. to make a P—B solution. Lithium hydroxide (40 g, 1 mole) is dissolved in in 1 L of water at 70° C. to form a Li solution. The P—B and Li solutions are mixed with stirring to precipitate out a crude lithium phosphate. Following complete precipitation, the crude product is collected by vacuum filtration, and then washed three times with 1 L of water at 70° C. to remove the excess sodium. The lithium phosphate is then dried overnight in a vacuum oven at 140° C. to obtain Catalyst 1A. Catalyst 1A contains 0.406 wt. % B. Typical yield is 120-125 g.

Comparative Catalyst 1B (700 ppm Na): Lithium phosphate containing 700 ppm sodium is prepared according to the procedure of Catalyst 1A except that the is crude lithium phosphate is washed five times with 1 L of water at 70° C. to remove the excess sodium. Comparative Catalyst 1B contains 0.470 wt. % B. Typical yield is 120-125 g.

Example 2

Isomerization of Propylene Oxide

Allyl alcohol is produced by isomerizing propylene oxide using lithium phosphate catalysts 1A and 1B according to the following procedure:

The isomerization is performed in a glass reactor, consisting of a cylindrical tube (3.8 cm ID, 17.8 cm length) that is connected to a 250-mL round expansion flask that sits above the tube. The expansion flask is fitted with a water-cooled condenser which is connected to a 250-mL receiving flask. The receiving flask is maintained at a temperature of 10° C. or lower. The reactor is fitted with a porous frit at the bottom of the cylindrical tube and an entrance port below the frit. To initiate reaction, a lithium phosphate catalyst slurry, consisting of 6-9 grams of catalyst in 65 grams of an appropriate heat transfer fluid (such as Therminol® 55 a product of Solutia, Inc.), is charged into the glass tube above the frit. Propylene oxide, vaporized in a preheating zone, is introduced into the bottom of the reactor at a constant rate (16.6 g/hr). The reaction is performed in the cylindrical tube at temperatures varying between 244-274° C. in the presence of the catalyst slurry.

The isomerization product mixture is condensed and collected in the receiving flask for each isomerization run. Product samples are periodically taken from the receiving flask and analyzed by GC for the propylene oxide conversion and allyl alcohol selectivity. The results are shown in Table 1. The results show that Catalyst 1A maintains a much higher selectivity to allyl alcohol at less than 37% PO conversion compared to Comparative Catalyst 1B which shows a steep decline in AA selectivity.

TABLE 1

PO Isomerization Comparison

| PO Conversion % | AA Selectivity (%) | |
| --- | --- | --- |
| | Catalyst 1A | Catalyst 1B* |
| 58.6 | 92.6 | — |
| 55.7 | — | 90.5 |
| 45.6 | 92.5 | — |
| 44.7 | — | 89.2 |
| 38.2 | 91.5 | — |
| 37.1 | — | 88.4 |
| 34.8 | — | 87.5 |
| 34.7 | 92.0 | — |
| 33.9 | 91.7 | — |
| 32.7 | — | 86.0 |
| 32.2 | 91.8 | — |
| 30.4 | 91.7 | — |
| 30.1 | — | 85.0 |
| 28.6 | 88.4 | — |
| 28.2 | — | 82.3 |
| 27.7 | — | 80.3 |
| 27.3 | 88.3 | — |
| 26.8 | — | 78.1 |
| 25.8 | 87.6 | — |

*Comparative Example

I claim:

1. A process to produce allyl alcohol comprising isomerizing propylene oxide, at a propylene oxide conversion of 37 percent or lower, in the presence of a lithium phosphate catalyst which contains boron and from 2000 to 4000 ppm sodium.

2. The process of claim 1 wherein the lithium phosphate catalyst contains from 2500 to 3500 ppm sodium.

3. The process of claim 1 wherein the lithium phosphate catalyst contains from 0.03 wt % to 1 wt % of boron.

4. The process of claim 1 wherein the lithium phosphate catalyst contains from 0.1 wt % to 0.8 wt % of boron.

5. The process of claim 1 wherein the isomerization is performed in slurry phase.

6. The process of claim 5 wherein the isomerization is performed in the presence of a $C_{12}$ or greater alkylaromatic hydrocarbon.

7. The process of claim 5 wherein the isomerization is performed at a temperature within the range of 200° C. to 300° C.

8. The process of claim 1 wherein the isomerization is performed in gas phase.

9. The process of claim 8 wherein the isomerization is performed at a temperature within the range of 150° C. to 400° C.

* * * * *